(12) United States Patent
Donath et al.

(10) Patent No.: US 9,474,781 B2
(45) Date of Patent: Oct. 25, 2016

(54) METHOD FOR INHIBITING CELL DEATH DURING LIVER FAILURE BY ADMINISTERING A CASPASE RECRUITMENT DOMAIN

(75) Inventors: Stefan Donath, Berlin (DE); Junfeng An, Berlin (DE)

(73) Assignee: Max-Delbruck-Centrum Fur Molekulare Medizin Berlin-Buch, Berlin (DE)

( * ) Notice: Subject to any disclaimer, the term of this patent is extended or adjusted under 35 U.S.C. 154(b) by 208 days.

(21) Appl. No.: 13/496,200

(22) PCT Filed: Sep. 15, 2010

(86) PCT No.: PCT/EP2010/063540
§ 371 (c)(1),
(2), (4) Date: Sep. 28, 2012

(87) PCT Pub. No.: WO2011/032981
PCT Pub. Date: Mar. 24, 2011

(65) Prior Publication Data
US 2013/0012455 A1    Jan. 10, 2013

(30) Foreign Application Priority Data
Sep. 15, 2009 (EP) .................................... 09011758

(51) Int. Cl.
*A61K 38/00* (2006.01)
*A61K 38/17* (2006.01)
*A61K 48/00* (2006.01)

(52) U.S. Cl.
CPC ......... *A61K 38/1709* (2013.01); *A61K 48/005* (2013.01)

(58) Field of Classification Search
None
See application file for complete search history.

(56) References Cited

U.S. PATENT DOCUMENTS 6,348,573 B1    2/2002 Nunez

OTHER PUBLICATIONS

Gustafsson et al. TAT protein transduction into isolated perfused hearts TAT-apoptosis repressor with caspase recruitment domain is cardioprotective. Circulation. 106:735-739, 2002.*
Bowie et al. Deciphering the message in protein sequences:tolerance to amino acid substitutions. Science, 247:1306-1310, 1990.*
Whisstock et al. Prediction of protein function from protein sequence and structure.Quarterly Reviews in Biophysics. 36(3):307-340, 2003.*
Koseki et al., "ACR, an inhibitor . . . caspases," PNAS 95:5156-5160, 1998.
Gustafsson et al., "TAT protein . . . cardioprotective," Circ 106:735-739, 2002.
Stravitz & Kramer, "Management of acute liver failure," Nat Rev Gastro Hep 6:542-553, 2009.

* cited by examiner

*Primary Examiner* — Prema Mertz
(74) *Attorney, Agent, or Firm* — MDIP LLC

(57) ABSTRACT

The invention refers to the use of a polynucleotide encoding "apoptosis repressor with caspase recruitment domain" (ARC) or a functional fragment thereof, and/or an ARC polypeptide or a functional fragment thereof for inhibiting cell death of a liver cell, in particular during liver failure.

6 Claims, 5 Drawing Sheets

SEQUENCE LISTING

```
<160> NUMBER OF SEQ ID NOS: 22

<210> SEQ ID NO 1
<211> LENGTH: 627
<212> TYPE: DNA
<213> ORGANISM: Homo sapiens

<400> SEQUENCE: 1
atgggcaacg cgcaggagcg gccgtcagag actatcgacc gcgagcggaa acgcctggtc      60
gagacgctgc aggcggactc gggactgctg ttggacgcgc tgctggcgcg gggcgtgctc     120
accgggccag agtacgaggc attggatgca ctgcctgatg ccgagcgcag ggtgcgccgc     180
ctactgctgc tggtgcaggg caagggcgag gccgcctgcc aggagctgct acgctgtgcc     240
cagcgtaccg cgggcgcgcc ggaccccgct tgggactggc agcacgtggg tccgggctac     300
cgggaccgca gctatgaccc tccatgccca ggccactgga cgccggaggc acccggctcg     360
gggaccacat gccccgggtt gcccagagct tcagaccctg acgaggccgg gggccctgag     420
ggctccgagg cggtgcaatc cgggaccccg gaggagccag agccagagct ggaagctgag     480
gcctctaaag aggctgaacc ggagccggag ccagagccag agctggaacc cgaggctgaa     540
gcagaaccag agccggaact ggagccagaa ccggacccag agcccgagcc cgacttcgag     600
gaaagggacg agtccgaaga ttcctga                                        627

<210> SEQ ID NO 2
<211> LENGTH: 208
<212> TYPE: PRT
<213> ORGANISM: Homo sapiens

<400> SEQUENCE: 2

Met Gly Asn Ala Gln Glu Arg Pro Ser Glu Thr Ile Asp Arg Glu Arg
  1               5                  10                  15

Lys Arg Leu Val Glu Thr Leu Gln Ala Asp Ser Gly Leu Leu Leu Asp
             20                  25                  30

Ala Leu Leu Ala Arg Gly Val Leu Thr Gly Pro Glu Tyr Glu Ala Leu
         35                  40                  45

Asp Ala Leu Pro Asp Ala Glu Arg Arg Val Arg Arg Leu Leu Leu Leu
     50                  55                  60

Val Gln Gly Lys Gly Glu Ala Ala Cys Gln Glu Leu Leu Arg Cys Ala
```

```
                65                  70                  75                  80
Gln Arg Thr Ala Gly Ala Pro Asp Pro Ala Trp Asp Trp Gln His Val
                    85                  90                  95
Gly Pro Gly Tyr Arg Asp Arg Ser Tyr Asp Pro Pro Cys Pro Gly His
                100                 105                 110
Trp Thr Pro Glu Ala Pro Gly Ser Gly Thr Thr Cys Pro Gly Leu Pro
                115                 120                 125
Arg Ala Ser Asp Pro Asp Glu Ala Gly Gly Pro Glu Gly Ser Glu Ala
                130                 135                 140
Val Gln Ser Gly Thr Pro Glu Glu Pro Glu Pro Glu Leu Glu Ala Glu
145                 150                 155                 160
Ala Ser Lys Glu Ala Glu Pro Glu Pro Glu Pro Glu Pro Glu Leu Glu
                165                 170                 175
Pro Glu Ala Glu Ala Glu Pro Glu Pro Glu Leu Glu Pro Glu Pro Asp
                180                 185                 190
Pro Glu Pro Glu Pro Asp Phe Glu Glu Arg Asp Glu Ser Glu Asp Ser
                195                 200                 205
```

<210> SEQ ID NO 3
<211> LENGTH: 627
<212> TYPE: DNA
<213> ORGANISM: Homo sapiens

<400> SEQUENCE: 3

| | | |
|---|---|---|
| atgggcaacg cgcaggagcg gccgtcagag actatcgacc gcgagcggaa acgcctggtc | 60 |
| gagacgctgc aggcggactc gggactgctg ttggacgcgc tgctggcgcg gggcgtgctc | 120 |
| accgggccag agtacgaggc attggatgca ctgcctgatg ccgagcgcag ggtgcgccgc | 180 |
| ctactgctgc tggtgcaggg caagggcgag gccgcctgcc aggagctgct acgctgtgcc | 240 |
| cagcgtaccg cgggcgcgcc ggaccccgct tgggactggc agcacgtggg tccgggctac | 300 |
| cgggaccgca gctatgaccc tccatgccca ggcactgga cgccgaggc accggctcg | 360 |
| gggaccacat gccccgggtt gcccagagct tcagaccctg acgaggccgg ggccctgag | 420 |
| ggctccgagg cggtgcaatc cggggacccg gaggagccag agccagagct ggaagctgag | 480 |
| gcctctaaag aggctgaacc ggagccggag ccagagccag agctggaacc cgaggctgaa | 540 |
| gcagaaccag agccggaact ggagccgaaa ccggacccag agcccgagcc cgacttcgag | 600 |
| gaaagggacg agtccgaaga ttcctga | 627 |

<210> SEQ ID NO 4
<211> LENGTH: 627
<212> TYPE: DNA
<213> ORGANISM: Artificial
<220> FEATURE:
<223> OTHER INFORMATION: mutated ARC

<400> SEQUENCE: 4

| | | |
|---|---|---|
| atgggcaacg cgcaggagcg gccgtcagag actatcgacc gcgagcggag acgcctggtc | 60 |
| gagacgctgc aggcggactc gggactgctg ttggacgcgc tgctggcgcg gggcgtgctc | 120 |
| accgggccag agtacgaggc attggatgca ctgcctgatg ccgagcgcag ggtgcgccgc | 180 |
| ctactgctgc tggtgcaggg caggggcgag gccgcctgcc aggagctgct acgctgtgcc | 240 |
| cagcgtaccg cgggcgcgcc ggaccccgct tgggactggc agcacgtggg tccgggctac | 300 |
| cgggaccgca gctatgaccc tccatgccca ggcactgga cgccgaggc accggctcg | 360 |
| gggaccacat gccccgggtt gcccagagct tcagaccctg acgaggccgg ggccctgag | 420 |

```
ggctccgagg cggtgcaatc cgggaccccg gaggagccag agccagagct ggaagctgag      480
gcctctagag aggctgaacc ggagccggag ccagagccag agctggaacc cgaggctgaa      540
gcagaaccag agccggaact ggagccagaa ccggacccag agcccgagcc cgacttcgag      600
gaaagggacg agtccgaaga ttcctga                                          627
```

<210> SEQ ID NO 5
<211> LENGTH: 208
<212> TYPE: PRT
<213> ORGANISM: Artificial
<220> FEATURE:
<223> OTHER INFORMATION: mutated ARC

<400> SEQUENCE: 5

```
Met Gly Asn Ala Gln Glu Arg Pro Ser Glu Thr Ile Asp Arg Glu Arg
1               5                   10                  15

Arg Arg Leu Val Glu Thr Leu Gln Ala Asp Ser Gly Leu Leu Leu Asp
            20                  25                  30

Ala Leu Leu Ala Arg Gly Val Leu Thr Gly Pro Glu Tyr Glu Ala Leu
        35                  40                  45

Asp Ala Leu Pro Asp Ala Glu Arg Arg Val Arg Arg Leu Leu Leu Leu
    50                  55                  60

Val Gln Gly Arg Gly Glu Ala Ala Cys Gln Glu Leu Leu Arg Cys Ala
65                  70                  75                  80

Gln Arg Thr Ala Gly Ala Pro Asp Pro Ala Trp Asp Trp Gln His Val
                85                  90                  95

Gly Pro Gly Tyr Arg Asp Arg Ser Tyr Asp Pro Cys Pro Gly His
            100                 105                 110

Trp Thr Pro Glu Ala Pro Gly Ser Gly Thr Thr Cys Pro Gly Leu Pro
        115                 120                 125

Arg Ala Ser Asp Pro Asp Glu Ala Gly Gly Pro Glu Gly Ser Glu Ala
    130                 135                 140

Val Gln Ser Gly Thr Pro Glu Glu Pro Glu Leu Glu Ala Glu
145                 150                 155                 160

Ala Ser Arg Glu Ala Glu Pro Glu Pro Glu Pro Glu Pro Glu Leu Glu
                165                 170                 175

Pro Glu Ala Glu Ala Glu Pro Glu Pro Glu Leu Glu Pro Glu Pro Asp
            180                 185                 190

Pro Glu Pro Glu Pro Asp Phe Glu Glu Arg Asp Glu Ser Glu Asp Ser
        195                 200                 205
```

<210> SEQ ID NO 6
<211> LENGTH: 627
<212> TYPE: DNA
<213> ORGANISM: Artificial
<220> FEATURE:
<223> OTHER INFORMATION: mutated ARC

<400> SEQUENCE: 6

```
atgggcaacg cgcaggagcg gccgtcagag actatcgacc gcgagcggag acgcctggtc      60
gagacgctgc aggcggactc gggactgctg ttggacgcgc tgctggcgcg gggcgtgctc     120
accgggccag agtacgaggc attggatgca ctgcctgatg ccgagcgcag ggtgcgccgc     180
ctactgctgc tggtgcaggg caggggcgag gccgcctgcc aggagctgct acgctgtgcc     240
cagcgtaccg cgggcgcgcc ggaccccgct tgggactgga gcacgtgggt ccgggctac      300 cgggaccgca gctatgaccc tccatgccca ggccactgga cgccggaggc acccggctcg     360
```

```
gggaccacat gccccgggtt gcccagagct tcagaccctg acgaggccgg gggccctgag      420
ggctccgagg cggtgcaatc cggggacccg gaggagccag agccagagct ggaagctgag      480
gcctctagag aggctgaacc ggagccggag ccagagccag agctggaacc cgaggctgaa      540
gcagaaccag agccggaact ggagccagaa ccggacccag agcccgagcc cgacttcgag      600
gaaagggacg agtccgaaga ttcctga                                          627
```

<210> SEQ ID NO 7
<211> LENGTH: 208
<212> TYPE: PRT
<213> ORGANISM: Artificial
<220> FEATURE:
<223> OTHER INFORMATION: mutated ARC

<400> SEQUENCE: 7

```
Met Gly Asn Ala Gln Glu Arg Pro Ser Glu Thr Ile Asp Arg Glu Arg
1               5                   10                  15

Arg Arg Leu Val Glu Thr Leu Gln Ala Asp Ser Gly Leu Leu Leu Asp
            20                  25                  30

Ala Leu Leu Ala Arg Gly Val Leu Thr Gly Pro Glu Tyr Glu Ala Leu
        35                  40                  45

Asp Ala Leu Pro Asp Ala Glu Arg Arg Val Arg Leu Leu Leu Leu
    50                  55                  60

Val Gln Gly Arg Gly Glu Ala Ala Cys Gln Glu Leu Leu Arg Cys Ala
65                  70                  75                  80

Gln Arg Thr Ala Gly Ala Pro Asp Pro Ala Trp Asp Trp Gln His Val
                85                  90                  95

Gly Pro Gly Tyr Arg Asp Arg Ser Tyr Asp Pro Pro Cys Pro Gly His
            100                 105                 110

Trp Thr Pro Glu Ala Pro Gly Ser Gly Thr Thr Cys Pro Gly Leu Pro
        115                 120                 125

Arg Ala Ser Asp Pro Asp Glu Ala Gly Gly Pro Glu Gly Ser Glu Ala
    130                 135                 140

Val Gln Ser Gly Asp Pro Glu Glu Pro Glu Pro Glu Leu Glu Ala Glu
145                 150                 155                 160

Ala Ser Arg Glu Ala Glu Pro Glu Pro Glu Pro Glu Pro Glu Leu Glu
                165                 170                 175

Pro Glu Ala Glu Ala Glu Pro Glu Pro Glu Leu Glu Pro Glu Pro Asp
            180                 185                 190

Pro Glu Pro Glu Pro Asp Phe Glu Glu Arg Asp Glu Ser Glu Asp Ser
        195                 200                 205
```

<210> SEQ ID NO 8
<211> LENGTH: 984
<212> TYPE: DNA
<213> ORGANISM: Artificial
<220> FEATURE:
<223> OTHER INFORMATION: expression construct for ARC

<400> SEQUENCE: 8

```
atctcgatcc cgcgaaatta atacgactca ctatagggag accacaacgg tttccctcta       60
gataattttg tttaacttta agaaggagat atacatatgc ggggttctca tcatcatcat      120
catcatggta tggctagcat gactggtgga cagcaaatgg gtcgggatct gtacgacgat      180
gacgataagg atcgatgggg atccaagctt ggctacggcc gcaagaaacg ccgccagcgc      240
cgccgcggtg gatccaccat ggccatgtcc ggctatccat atgacgtccc agactatgct      300
```

```
ggctccatgg ccggtaccat gggcaacgcg caggagcggc cgtcagagac tatcgaccgc    360
gagcggaaac gcctggtcga gacgctgcag gcggactcgg gactgctgtt ggacgcgctg    420
ctggcgcggg gcgtgctcac cgggccagag tacgaggcat tggatgcact gcctgatgcc    480
gagcgcaggg tgcgccgcct actgctgctg gtgcagggca agggcgaggc cgcctgccag    540
gagctgctac gctgtgccca gcgtaccgcg ggcgcgccgg accccgcttg ggactggcag    600
cacgtgggtc cgggctaccg ggaccgcagc tatgaccctc catgcccagg ccactggacg    660
ccggaggcac ccggctcggg gaccacatgc cccgggttgc ccagagcttc agaccctgac    720
gaggccgggg gccctgaggg ctccgaggcg gtgcaatccg gaccccgga ggagccagag     780 ccagagctgg aagctgaggc ctctaaagag ctgaaccgg agccggagcc agagccagag     840
ctggaacccg aggctgaagc agaaccagac cggaactgg agccagaacc ggacccagag     900
cccgagcccg acttcgagga aagggacgag tccgaagatt cctgaggtac cggtctcgag    960
gtgcatgcgg tgaattcgaa gctt                                           984
```

<210> SEQ ID NO 9
<211> LENGTH: 282
<212> TYPE: PRT
<213> ORGANISM: Homo sapiens

<400> SEQUENCE: 9

```
Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Lys Leu Gly Tyr Gly Arg Lys Lys Arg Gln Arg
        35                  40                  45

Arg Arg Gly Gly Ser Thr Met Ala Met Ser Gly Tyr Pro Tyr Asp Val
    50                  55                  60

Pro Asp Tyr Ala Gly Ser Met Ala Gly Thr Met Gly Asn Ala Gln Glu
65                  70                  75                  80

Arg Pro Ser Glu Thr Ile Asp Arg Glu Arg Lys Arg Leu Val Glu Thr
                85                  90                  95

Leu Gln Ala Asp Ser Gly Leu Leu Leu Asp Ala Leu Leu Ala Arg Gly
            100                 105                 110

Val Leu Thr Gly Pro Glu Tyr Glu Ala Leu Asp Ala Leu Pro Asp Ala
        115                 120                 125

Glu Arg Arg Val Arg Arg Leu Leu Leu Leu Val Gln Gly Lys Gly Glu
    130                 135                 140

Ala Ala Cys Gln Glu Leu Leu Arg Cys Ala Gln Arg Thr Ala Gly Ala
145                 150                 155                 160

Pro Asp Pro Ala Trp Asp Trp Gln His Val Gly Pro Gly Tyr Arg Asp
                165                 170                 175

Arg Ser Tyr Asp Pro Pro Cys Pro Gly His Trp Thr Pro Glu Ala Pro
            180                 185                 190

Gly Ser Gly Thr Thr Cys Pro Gly Leu Pro Arg Ala Ser Asp Pro Asp
        195                 200                 205

Glu Ala Gly Gly Pro Glu Gly Ser Glu Ala Val Gln Ser Gly Thr Pro
    210                 215                 220

Glu Glu Pro Glu Pro Glu Leu Glu Ala Glu Ala Ser Lys Glu Ala Glu
225                 230                 235                 240

Pro Glu Pro Glu Pro Glu Pro Glu Leu Glu Pro Glu Ala Glu Ala Glu
```

```
                          245                 250                 255
Pro Glu Pro Glu Leu Glu Pro Glu Pro Asp Pro Glu Pro Glu Pro Asp
            260                 265                 270

Phe Glu Glu Arg Asp Glu Ser Glu Asp Ser
            275                 280
```

<210> SEQ ID NO 10
<211> LENGTH: 177
<212> TYPE: DNA
<213> ORGANISM: human immunodificiency virus

<400> SEQUENCE: 10

```
atgcggggtt ctggtatggc tagcatgact ggtggacagc aaatgggtcg ggatctgtac      60
gacgatgacg ataaggatcg atggggatcc aagcttggct acggccgcaa gaaacgccgc     120
cagcgccgcc gcggtggatc caccatggcc atgtccggcg ctccatggc cggtacc         177
```

<210> SEQ ID NO 11
<211> LENGTH: 59
<212> TYPE: PRT
<213> ORGANISM: human immunodificiency virus

<400> SEQUENCE: 11

```
Met Arg Gly Ser Gly Met Ala Ser Met Thr Gly Gly Gln Gln Met Gly
1               5                   10                  15

Arg Asp Leu Tyr Asp Asp Asp Asp Lys Asp Arg Trp Gly Ser Lys Leu
            20                  25                  30

Gly Tyr Gly Arg Lys Lys Arg Arg Gln Arg Arg Gly Gly Ser Thr
        35                  40                  45

Met Ala Met Ser Gly Gly Ser Met Ala Gly Thr
    50                  55
```

<210> SEQ ID NO 12
<211> LENGTH: 804
<212> TYPE: DNA
<213> ORGANISM: Artificial
<220> FEATURE:
<223> OTHER INFORMATION: fusion construct

<400> SEQUENCE: 12

```
atgcggggtt ctggtatggc tagcatgact ggtggacagc aaatgggtcg ggatctgtac      60
gacgatgacg ataaggatcg atggggatcc aagcttggct acggccgcaa gaaacgccgc     120
cagcgccgcc gcggtggatc caccatggcc atgtccggcg ctccatggc cggtaccatg      180 ggcaacgcgc aggagcggcc gtcagagact atcgaccgcg agcggaaacg cctggtcgag     240
acgctgcagg cggactcggg actgctgttg gacgcgctgc tggcgcgggg cgtgctcacc     300
gggccagagt acgaggcatt ggatgcactg cctgatgccg agcgcagggt gcgccgccta     360
ctgctgctgg tgcagggcaa gggcgaggcc gcctgccagg agctgctacg ctgtgcccag     420
cgtaccgcgc gcgcgccgga ccccgcttgg gactggcagc acgtgggtcc gggctaccgg     480
gaccgcagct atgaccctcc atgcccaggc cactggacgc ggaggcacc cggctcgggg     540 accacatgcc ccgggttgcc cagagcttca gaccctgacg aggccggggg ccctgagggc     600
tccgaggcgg tgcaatccgg gaccccggag gagccagagc cagagctgga agctgaggcc     660
tctaaagagg ctgaaccgga gccggagcca gagccagagc tggaacccga ggctgaagca     720
gaaccagagc cggaactgga gccagaaccg gaccagagc ccgagcccga cttcgaggaa     780
agggacgagt ccgaagattc ctga                                            804
```

```
<210> SEQ ID NO 13
<211> LENGTH: 267
<212> TYPE: PRT
<213> ORGANISM: Artificial
<220> FEATURE:
<223> OTHER INFORMATION: fusion protein

<400> SEQUENCE: 13
```

| Met | Arg | Gly | Ser | Gly | Met | Ala | Ser | Met | Thr | Gly | Gly | Gln | Gln | Met | Gly |
|---|---|---|---|---|---|---|---|---|---|---|---|---|---|---|---|
| 1 | | | | 5 | | | | | 10 | | | | | 15 | |

| Arg | Asp | Leu | Tyr | Asp | Asp | Asp | Lys | Asp | Arg | Trp | Gly | Ser | Lys | Leu |
|---|---|---|---|---|---|---|---|---|---|---|---|---|---|---|
| | | | 20 | | | | 25 | | | | 30 | | | |

Gly Tyr Gly Arg Lys Lys Arg Gln Arg Arg Gly Gly Ser Thr
            35              40              45

Met Ala Met Ser Gly Gly Ser Met Ala Gly Thr Met Gly Asn Ala Gln
 50              55              60

Glu Arg Pro Ser Glu Thr Ile Asp Arg Glu Arg Lys Arg Leu Val Glu
65              70              75              80

Thr Leu Gln Ala Asp Ser Gly Leu Leu Leu Asp Ala Leu Leu Ala Arg
                85              90              95

Gly Val Leu Thr Gly Pro Glu Tyr Glu Ala Leu Asp Ala Leu Pro Asp
            100             105             110

Ala Glu Arg Arg Val Arg Arg Leu Leu Leu Leu Val Gln Gly Lys Gly
            115             120             125

Glu Ala Ala Cys Gln Glu Leu Leu Arg Cys Ala Gln Arg Thr Ala Gly
130             135             140

Ala Pro Asp Pro Ala Trp Asp Trp Gln His Val Gly Pro Gly Tyr Arg
145             150             155             160

Asp Arg Ser Tyr Asp Pro Pro Cys Pro Gly His Trp Thr Pro Glu Ala
                165             170             175

Pro Gly Ser Gly Thr Thr Cys Pro Gly Leu Pro Arg Ala Ser Asp Pro
            180             185             190

Asp Glu Ala Gly Gly Pro Glu Gly Ser Glu Ala Val Gln Ser Gly Thr
            195             200             205

Pro Glu Glu Pro Glu Pro Glu Leu Glu Ala Glu Ala Ser Lys Glu Ala
    210             215             220

Glu Pro Glu Pro Glu Pro Glu Leu Glu Pro Glu Ala Glu Ala
225             230             235             240

Glu Pro Glu Pro Glu Leu Glu Pro Glu Pro Asp Pro Glu Pro Glu Pro
            245             250             255

Asp Phe Glu Glu Arg Asp Glu Ser Glu Asp Ser
            260             265

```
<210> SEQ ID NO 14
<211> LENGTH: 11
<212> TYPE: PRT
<213> ORGANISM: Homo sapiens

<400> SEQUENCE: 14
```

Tyr Gly Arg Lys Lys Arg Arg Gln Arg Arg Arg
1               5                   10

```
<210> SEQ ID NO 15
<211> LENGTH: 33
<212> TYPE: DNA
<213> ORGANISM: Homo sapiens
```

```
<400> SEQUENCE: 15
tacggccgca agaaacgccg ccagcgccgc cgc                                   33

<210> SEQ ID NO 16
<211> LENGTH: 19
<212> TYPE: PRT
<213> ORGANISM: Drosophila

<400> SEQUENCE: 16

Ser Gly Arg Gln Ile Lys Ile Trp Phe Gln Asn Arg Arg Met Lys Trp
1               5                   10                  15

Lys Lys Cys

<210> SEQ ID NO 17
<211> LENGTH: 12
<212> TYPE: PRT
<213> ORGANISM: unknown
<220> FEATURE:
<223> OTHER INFORMATION: PTD

<400> SEQUENCE: 17

Arg Arg Gln Arg Arg Thr Ser Lys Leu Met Lys Arg
1               5                   10

<210> SEQ ID NO 18
<211> LENGTH: 9
<212> TYPE: PRT
<213> ORGANISM: unknown
<220> FEATURE:
<223> OTHER INFORMATION: PTD

<400> SEQUENCE: 18

Arg Arg Arg Arg Arg Arg Arg Arg Arg
1               5

<210> SEQ ID NO 19
<211> LENGTH: 11
<212> TYPE: PRT
<213> ORGANISM: unknown
<220> FEATURE:
<223> OTHER INFORMATION: PTD

<400> SEQUENCE: 19

Tyr Ala Arg Ala Ala Ala Arg Gln Ala Arg Ala
1               5                   10

<210> SEQ ID NO 20
<211> LENGTH: 8
<212> TYPE: PRT
<213> ORGANISM: unknown
<220> FEATURE:
<223> OTHER INFORMATION: PTD

<400> SEQUENCE: 20

Arg Arg Arg Arg Arg Arg Arg Arg
1               5

<210> SEQ ID NO 21
<211> LENGTH: 8
<212> TYPE: PRT
<213> ORGANISM: unknown
<220> FEATURE:
<223> OTHER INFORMATION: PTD
```

-continued

```
<400> SEQUENCE: 21

Lys Lys Lys Lys Lys Lys Lys Lys
1               5

<210> SEQ ID NO 22
<211> LENGTH: 9
<212> TYPE: PRT
<213> ORGANISM: unknown
<220> FEATURE:
<223> OTHER INFORMATION: PTD

<400> SEQUENCE: 22

Lys Lys Lys Lys Lys Lys Lys Lys Lys
1               5
```

METHOD FOR INHIBITING CELL DEATH DURING LIVER FAILURE BY ADMINISTERING A CASPASE RECRUITMENT DOMAIN

SEQUENCE LISTING

The instant application contains a Sequence Listing submitted herewith electronically in ASCII format and hereby is incorporated by reference in entirety. Said ASCII copy, created on 8 Apr. 2014, is named NewSL.txt and is 22,002 bytes in size.

The invention relates to the use of a polynucleotide encoding apoptosis repressor with caspase recruitment domain (ARC) or a functional fragment thereof, and/or an ARC polypeptide or a functional fragment thereof for inhibiting cell death of a liver cell as it occurs in e.g. acute liver failure (ALF).

INTRODUCTION

Liver failure, in particular acute liver failure (ALF) is associated with massive hepatocyte cell death and high mortality rates (1, 2). Therapeutic approaches targeting hepatocyte cell death in acute liver failure are hampered by the activation of diverse stimulus-dependent signalling pathways and modes of cell death.

Liver failure, in particular acute liver failure (ALF) is a syndrome of diverse etiology, in which patients without previously recognized liver disease sustain a liver injury that results in rapid loss of hepatic function. Depending on the etiology and severity of the insult, some patients undergo rapid hepatic regeneration and spontaneously recover. However, nearly 60% of patients with ALF in the US require and undergo orthotopic liver transplantation or die (2).

Common causes for acute liver failure are paracetamol (acetaminophen) overdose, α-amanitin intoxication, idiosyncratic reaction to medication (e.g. tetracycline, troglitazone), viral hepatitis, excessive alcohol intake, acute fatty liver of pregnancy, and idiopathic. Reye syndrome is acute liver failure in a child with a viral infection. Furthermore, Wilson's disease (hereditary copper accumulation) may infrequently present with acute liver failure.

The apoptosis repressor with caspase recruitment domain (ARC) is a recently discovered death repressor that interferes with death receptor and mitochondrial apoptotic signalling by multiple protein-protein interactions.

TAT-ARC, a fusion protein consisting of the HIV TAT protein and the above-mentioned ARC protein was shown to be cardioprotective in a rat model, which was a model of ischemia-reperfusion injury, simulating a myocardial infarction (3).

Figure 1:
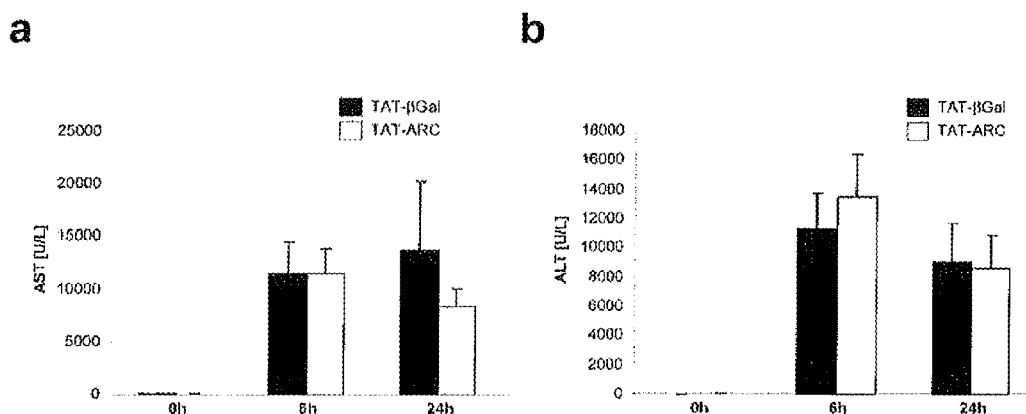

The inventors initially investigated whether ARC was also able to rescue liver cells from cell death in a partial hepatic ischemia-reperfusion injury animal model (FIG. 1). In contrast to the results published for the heart, no reduction of transaminases was found, which would have been indicative for a decrease of cell death in the liver.

Figure 5:
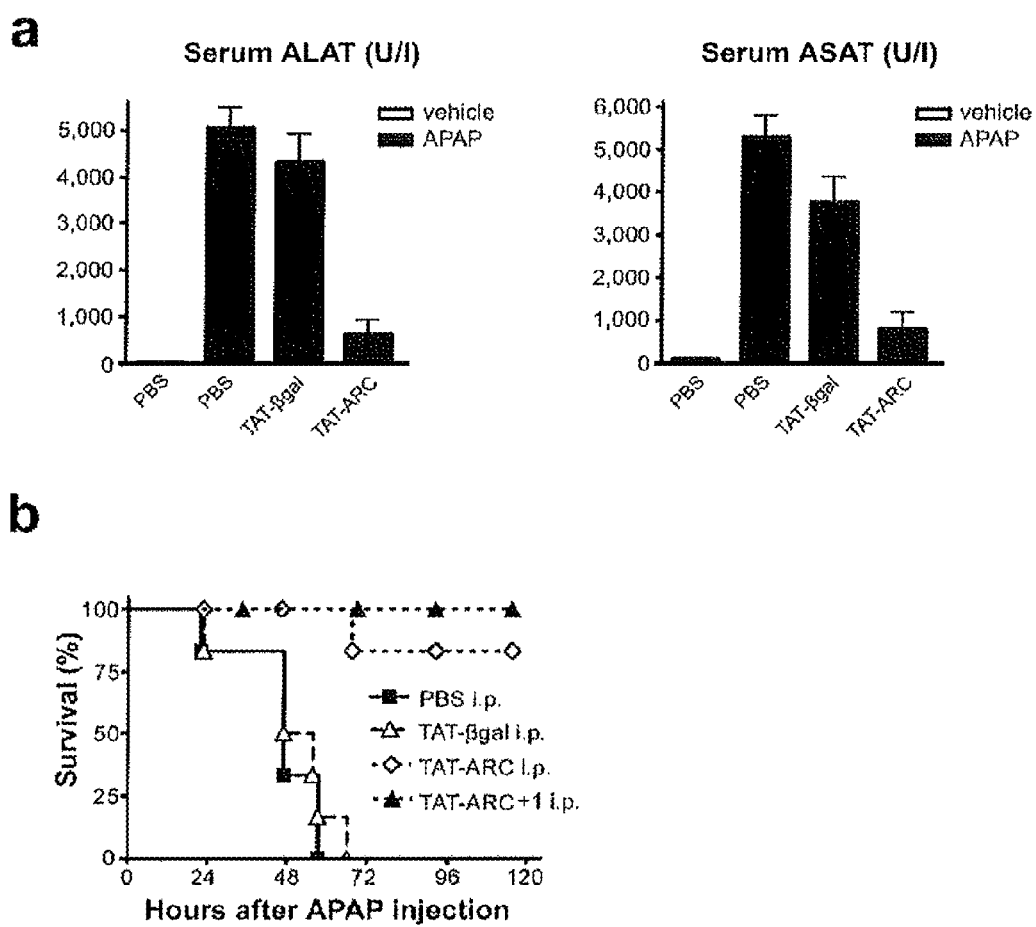

The reasons for the different response of the heart and the liver to a decreased blood perfusion are not yet understood and might be manifold. For one, different signal transduction mechanisms might be involved in the demise of the respective cells in the heart and the liver. Also, endogenous ARC protein was shown to be expressed in the heart, whereas no ARC expression was found in liver cells (FIG. 5). Furthermore, knockdown of ARC in heart muscle cells leads to spontaneous cardiomyocyte death. Therefore it seems that ARC expression levels are essential for cardiac tissue homeostasis under physiological conditions whereas they are of no relevance in liver cells.

Based on this, it comes as a surprise that the inventors have found that ARC is capable of inhibiting cell death during acute liver failure.

In addition to the prior art documents mentioned above, the following documents are of relevance: WO 99/55134 describes compositions and methods for identifying apoptosis signalling pathways inhibitors and activators. Koseki at al. (PNAS, 95: 5156-5160, 1998) describes ARC as an inhibitor of apoptosis expressed in skeletal muscle and heart that interacts with caspases.

DESCRIPTION

In one aspect, the invention pertains to the use of a polynucleotide including the ARC protein or a functional fragment thereof as well as the use of an ARC polypeptide or a functional fragment thereof for inhibiting the cell death of the liver cell, in particular during liver failure, preferably during acute liver failure (ALF).

Acute liver failure is the appearance of severe complications rapidly after the first signs of liver disease (such as jaundice), and indicates that the liver has sustained severe damage. The complications are hepatic encephalopathy and impaired protein synthesis. The 1993 classification defines hyperacute as within 1 week, acute as 8-28 days and subacute as 4 to 12 weeks (4). It reflects the fact that the pace of disease evolution strongly influences prognosis. The term "acute liver failure" as used herein refers to hyperacute, acute, and subacute stages as defined above. Accordingly, the invention refers to treating or preventing liver failure or acute liver failure within 1 to 12 weeks after the first signs of liver disease. In a preferred embodiment, the invention refers to treating or preventing liver failure or acute liver failure from 1 to 12, most preferably from 1 to 4 weeks after the first signs of liver disease.

A polynucleotide (DNA) encoding the ARC protein (SEQ ID NO. 2) is shown as SEQ ID NO. 1. The RNA sequence corresponding to the DNA sequence denoted SEQ ID NO. 1 can be deduced from the DNA sequence by a person of skill in the art, such as from all other DNA sequences disclosed herein. Thus, the term polynucleotide can refer to both DNA and RNA. A functional ARC fragment is a fragment of the complete ARC protein according to SEQ ID NO. 1 that shows a statistically significant and reproducible decrease of the death of the liver cell during liver failure, in particular during acute liver failure.

Several assays can be used to determine whether a fragment of the ARC protein (or of a TAT-ARC protein) is a functional fragment. For example, immunoprecipitation of the ARC fragment with proteins interacting with ARC in vitro or in vivo, such as Fas, FADD, procaspase-8, BAX, or BAD can be used. Further, following ARC expression in or transduction into a liver cell and stimulation of the Fas- (Jo2) or TNF-alpha receptors, the caspase-8 activity or cell death using TUNEL assay can be measured as an indicator whether an ARC fragment is a functional fragment. Also, it is possible to measure the inhibition of cell death in H9c2 cells using a TUNEL assay following $H_2O_2$ stimulation and expression or transduction of an ARC fragment.

The invention can also be performed with a homolog of mutant of ARC with a sequence as shown in SEQ ID NO. 2. Preferred are homologs with a similarity of at least 70%, 80%, 85% 90%, 95%, 98%, or preferably 99%, as long as these homologs exhibit the same qualitative and/or quantitative function as ARC with a sequence as shown in SEQ ID NO. 2.

A functional domain of ARC is, for example, the caspase recruitment domain, CARD, which is defined by amino acids 5 to 92 of the sequence of SEQ ID NO. 1.

Further, several gain of function mutations of ARC can be used, e.g. ARC 149D (pseudo-phosphorylated ARC); or KR3 ARC (SEQ ID Nos. 3 and 5, respectively). ARC 149D (SEQ ID NO. 4) can be encoded e.g. by a polynucleotide of SEQ ID NO. 3. KR3 ARC (SEQ ID NO. 6) can be encoded e.g. by a polynucleotide of SEQ ID NO. 5. KR3 ARC 149D (SEQ ID NO. 8) can be encoded e.g. by a polynucleotide of SEQ ID NO. 7. Further polynucleotide encoding the respective polypeptides (proteins) can be deduced by a person of skill in the art based on the degenerate genetic code.

The invention can be used to prevent the cell death of a liver cell, both in vitro and in vivo. In this regard, the term "prevent" refers to the inhibition of cell death of a liver cell. One can also refer to an aspect of the invention as a treatment of a condition that leads to cell death of a liver cell, e.g. due to necroses and/or apoptosis, in particular to a treatment of liver failure or acute liver failure. The term "treat" refers to inhibiting activation or progression of cell death, e.g. as measured by cell death signalling, otherwise leading to cell death of a liver cell. Treatment my entail healing or curing of a subject, but may also refer to the achievement of amelioration of the subject's state of health with respect to his liver function.

In a preferred embodiment of the invention, the cell death of a liver cell during liver failure, preferably during liver failure and/or acute liver failure (ALF) is treated or prevented.

Cell Penetrating Peptides, also known as protein transduction domains (PTDs), are carriers with small peptide domains that can freely cross cell membranes. Several PTDs have been identified that allow a fused protein to efficiently cross cell membranes in a process known as protein transduction.

Preferably, in order to ensure the entrance of the ARC protein into the liver cell, ARC is being delivered into a liver cell, both in vitro and in vivo, as a fusion protein comprising a protein transduction domain (PTD), such as, e.g., the PTD of the human immunodeficiency virus (HIV) TAT protein, comprising the sequence YGRKKRRQRRR (shown as SEQ ID NO. 15, encoded e.g. by SEQ ID NO 16) (5-9). Mutations of this sequence are known in the state of the art. Therefore, it is possible to use mutations of the sequence according to SEQ ID NO. 15 as long as the function of the PTD is not lost. Preferred are sequences in which one to three amino acids of the sequence according to SEQ ID NO. 14 have been mutated. Accordingly, mutations of the polynucleotide encoding such a PTD can also be used.

Other possible PTDs (10-12) that can be used with the invention is the Drosophila Antennapedia PTD with the sequence SGRQIKIWFQNRRMKWKKC (SEQ ID NO. 17), or RRQRRTSKLMKR (SEQ ID NO. 18), RRRRRRRR (SEQ ID NO. 19), YARAAARQARA (SEQ ID NO. 20), RRRRRRRR (SEQ ID NO. 21), KKKKKKKK (SEQ ID NO. 22), or KKKKKKKKK (SEQ ID NO. 23) or any of these PTDs with a similarity of at least 80%, at least 85%, at least 90%, at least 95%, at least 98%, or at least 99%. Other PTDs are described in (13), which is, as all documents cited herein, hereby incorporated by reference.

The sequence according to SEQ ID NO. 15 is the PTD of TAT. A sequence comprising this TAT PTD is e.g. shown as SEQ ID NO. 12 that represents the whole TAT protein (encoded by the polynucleotide of SEQ ID NO. 11).

The TAT-ARC polynucleotide sequence shown as SEQ ID NO. 9, encodes for the TAT-ARC fusion protein with the KR3 ARC (SEQ ID NO. 6) of SEQ ID NO. 10.

A polynucleotide encoding TAT protein is shown as SEQ ID NO 11. A TAT-ARC polynucleotide sequence is shown as SEQ ID NO. 9, encoding for the TAT-ARC fusion protein with the KR3 ARC (SEQ ID NO. 6). The TAT-ARC polynucleotide sequence shown as SEQ ID NO. 9 encodes for a polypeptide of SEQ ID NO. 10.

A functional TAT-ARC fragment is a fragment of a protein comprising both TAT and ARC that shows a statistically significant and reproducible decrease of the liver cell death during liver failure, in particular during acute liver failure and is able to enter a human liver cell.

PTD is preferably located N-terminal with respect to the ARC protein. However, it is also possible to locate the PTD C-terminally with respect to the ARC protein. Both possible forms are denoted herein as PTD-ARC.

A person of skill in the art will appreciate that a polynucleotide sequence of the invention is preferably expressed in a suitable cell system such as bacteria or mammalian cells and the expressed protein is isolated and purified for delivery into the liver cell. The polynucleotide sequence may also be synthesized in a laboratory, i.e. outside a cellular system, e.g. using wet chemistry.

In order to simplify the isolation of the PTD-ARC fusion protein, a tag as known in the art for isolating the protein, such as the His-tag, HA-tag, etc. can be used.

The use of a polynucleotide comprising the PTD-ARC protein (such as the TAT-ARC protein) or a functional fragment thereof as well as the use of a PTD-ARC (such as the TAT-ARC) polypeptide or a functional fragment thereof for inhibiting the cell death of the liver cell, such as described above and herein, may comprise the provision of a liver cell, or liver tissue (in particular if performed in vitro) or of a liver and the introduction of polynucleotide including the ARC (or the PTD-ARC) protein or a functional fragment thereof for expressing ARC (or PTD-ARC) protein in the liver cell and/or the introduction of an ARC (or a PTD-ARC) polypeptide or a functional fragment thereof for inhibiting or preventing cell death of the liver cell. In case an ARC (or a PTD-ARC) polypeptide or a functional fragment thereof is introduced, it needs to be configured such that the expression of as ARC (or PTD-ARC) polypeptide or a functional fragment thereof is possible in the cell. For this reason, a promoter and/or transcription enhancing elements may be additionally provided. SEQ ID NO 9 shows a polynucleotide sequence of such a construct with a bacterial promoter, a His-tag, TAT, a HA-tag, ARC and a stop codon.

In another aspect of the invention, the polynucleotide encoding ARC (or PTD-ARC) or a functional fragment thereof and/or the ARC (or the PTD-ARC) polypeptide or a functional fragment thereof can be used for the manufacture of a medicament for inhibiting cell death of a liver cell, in particular during liver failure or acute liver failure. Such a medicament may comprise other substances known in the art, such as additives and/or pharmacological excipients.

In another aspect, the invention pertains to a polynucleotide encoding ARC (or PTD-ARC) or a functional fragment thereof and/or an ARC (or PTD-ARC) polypeptide or a functional fragment thereof for inhibiting the cell death of a liver cell, in particular during liver failure or acute liver failure.

In a further aspect, an ARC (or PTD-ARC) polypeptide or a functional fragment thereof can be used for inhibiting cell death of a liver cell, in particular during liver failure or acute liver failure.

Further, a polynucleotide or a construct, such as a vector or virus known in the art, containing such a polynucleotide encoding ARC or a functional fragment thereof can be used for inhibiting cell death of a liver cell, in particular during liver failure or acute liver failure.

Also, an ARC (or a PTD-ARC) polypeptide or a functional fragment thereof can be used for inhibiting cell death of a liver cell, in particular during liver failure or acute liver failure.

In another aspect, the invention refers to a medicament for preventing the death of a liver cell, in particular as it occurs during liver failure or acute liver failure. Such a medicament comprises a polynucleotide encoding ARC (or PTD-ARC) or a functional fragment thereof and/or an ARC (or a PTD-ARC) polypeptide or a functional fragment thereof (preferably a PTD-ARC polypeptide or a functional fragment thereof) for inhibiting cell death of a liver cell. Accordingly, a polynucleotide encoding ARC (or PTD-ARC) or a functional fragment thereof, and/or an ARC (or PTD-ARC) polypeptide or a functional fragment thereof can each be used for inhibiting death of a liver cell, in particular during liver failure or acute liver failure.

The medicament may contain other substances known in the art, such as additives and/or pharmacological excipients.

Further, the invention refers to a method, in particular an in vitro method for preventing the death of the liver cell, in particular as it occurs during liver failure or acute liver failure. In this aspect, the invention refers to a method for treating liver failure or acute liver failure. This method comprises expressing ARC in a liver cell or introducing ARC protein into the liver cell. The protein introduction of ARC is preferably done using a PTD-ARC fusion protein, such as TAT-ARC, as described herein. The introduction of a polynucleotide encoding ARC may be achieved through sonoporation, liposomes, viruses, viral proteins such as VP22 or Antennapedia or other protein transduction domains as known in the art.

When applying the ARC protein or the polynucleotide encoding ARC to a subject, such as a patient, who is preferably a human, a catheter may be used that is introduced into the body of the subject. In particular, the catheter can be introduced into a blood vessel, such as the Vena portae. When a protein is administered, such as the TAT-ARC fusion protein, the protein can be applied intraperitoneally or intravenously.

In the method for treating liver failure or acute liver failure, ARC polypeptide can be administered either as a protein or a protein component (e.g. as TAT-ARC) or a functional fragment thereof, or be administered as a polynucleotide encoding ARC or a functional fragment thereof.

The invention also pertains to a kit for inhibiting cell death of a liver cell, in particular during liver failure, comprising a polynucleotide encoding ARC (or PTD-ARC) or a functional fragment thereof, and/or an ARC (or PTD-ARC) polypeptide or a functional fragment thereof. The kit can e.g. be used for manufacturing a medicament for inhibiting cell death of a liver cell.

Instead of wild type ARC (or PTD-ARC) polypeptide or a functional fragment thereof, modified ARC (or PTD-ARC) or a modified functional fragment thereof can also be used according to the invention. Possible modifications are pegylation, glycosylation, the addition of a tag etc. as known in the art, as long as the qualitative and/or quantitative function of ARC is not annihilated by the modification. The wild type polynucleotide encoding ARC or a functional fragment thereof can also be modified. The polynucleotide may be a DNA, RNA, locked nucleic acid (LNA), morpholino, or peptide nucleic acid (PNA), etc. Combinations of the before mentioned polynucleotide are also possible.

Introduction of ARC or of an ARC derivative such as PTD-ARC into a liver cell can also be accomplished using e.g. liposomes (V. P. Torchilin, Recent advances with liposomes as pharmaceutical carriers, Nature Reviews Drug Discovery 2005: 4, 145-160), chemical or physical carriers, nanoparticles, etc. as known in the art. For in vitro use, electroporation, injection, liposomes, etc. can be used.

EXAMPLES

The effect of TAT-ARC as a PTD-ARC compared to TAT-βgal protein transduction was evaluated in an in vivo model of partial hepatic ischemia reperfusion injury. At 6 and 24 hours of reperfusion, transaminases were measured in the blood as a marker of liver injury. However, no significant effect was seen between the TAT-βgal and TAT-ARC treated group (FIGS. 1a & b).

In contrast to murine heart muscle, immunoblot analysis of ARC protein expression in hepatocytes and whole liver tissue lysates of human and murine origin showed no ARC expression (FIG. 2a). Because of the short therapeutic time window in otherwise lethal liver failure the inventors decided to utilize a protein therapy approach based on the protein transduction domain of HIV-1 TAT. TAT-ARC and TAT-βgal fusion proteins were generated. Relevant transduction of the fusion proteins was documented in several western blots showing strong ARC and βgal expression in liver tissue lysates following intraperitoneal injection (FIG. 2a-c).

Acute liver failure is characterized by a stimulus-dependent activation of Fas or TNF-receptor and mitochondrial death signaling pathways that lead to massive apoptotic and/or necrotic cell death.

To determine whether ARC protects from Fas-induced liver failure in vivo, Balb/c mice were injected intravenously with Fas-agonistic antibody, 2 hours following pre-treatment with intraperitoneal TAT-ARC, TAT-βgal, or PBS injection. In response to Fas stimulation TAT-βgal or PBS pre-treated mice died within 12 hours of acute liver failure associated with massive hepatic cellular damage as indicated by extensive increases in serum transaminase levels (FIGS. 3a & b). In contrast, all mice pre-treated with TAT-ARC fusion protein survived anti-Fas antibody injection with no apparent liver injury by determination of serum transaminase levels (FIGS. 3a & b). Remarkably, all mice survived intravenous anti-Fas antibody application even when TAT-ARC fusion protein was given 1 hour after Fas-agonistic stimulation (FIG. 3b).

TNF-alpha-induced hepatocyte death is implicated in a wide range of liver diseases including viral hepatitis, alcoholic hepatitis, ischemia/reperfusion liver injury, and fulminant hepatic failure. TNF-alpha-induced liver injury is mediated by multiple signaling events, which are yet to be fully revealed. The molecular basis of hepatocyte destruction in TNF-alpha-mediated hepatitis can be studied with mouse models. ConA-induced hepatitis is a TNF-alpha-dependent, T-cell mediated model for fulminant liver failure in humans. ConA exerts cytotoxic effects through secreted and cell-bound TNF-alpha, which activates type 1 and 2 TNF receptors. Secreted TNF-alpha also appears to be critical in the model of GalN/LPS-induced fatal hepatitis.

The inventors next examined whether TAT-ARC protein transduction protects mice from fulminant hepatitis induced by ConA or GalN/LPS. Mice treated with TAT-ARC, TAT-βgal, or PBS were challenged 2 hours later by an intravenous injection of ConA or intraperitoneal administration of GalN/LPS. Similar to Fas-agonistic antibody treated mice TAT-βgal and PBS-treated mice showed significantly elevated serum transaminases following ConA or GalN/LPS stimulation (FIG. 4a). In contrast, TAT-ARC also conferred resistance to ConA- and GalN/LPS-induced fulminant hepatitis (FIG. 4a). While ConA and GalN/LPS induced lethal fulminant hepatitis pretreatment and delayed administration of TAT-ARC rescued all treated animals (FIG. 4b).

Acetaminophen poisoning has become the most common cause of acute liver failure in the United States. Therefore, a mouse model of acetaminophen (APAP)-induced liver failure was used to test the effect of TAT-ARC protein transduction on liver injury and survival. 20 hours following APAP treatment TAT-ARC pretreated mice showed significantly less necrotic liver cell damage as determined by blood transaminase levels (FIG. 5a). As shown in FIG. 5b compared with control mice, survival of TAT-ARC treated mice was significantly enhanced in response to APAP intoxication.

Thus, the efficacy of ARC protein transduction, in particular of PDT-ARC, such as TAT-ARC protein transduction in multiple models of acute liver failure (Fas, ConA, GalN/LPS, APAP) shows its therapeutic efficacy for reversing human liver failure.

REFERENCES

1. Malhi H, Gores G J, Lemasters J J. Apoptosis and necrosis in the liver: a tale of two deaths? Hepatology 2006; 43: 31-44.
2. Stravitz R T, Kramer D J; Medscape. Management of acute liver failure. Nat Rev Gastroenterol Hepatol. 2009; 6(9): 542-553.
3. Gustafsson A B, Sayen M R, Williams S D, Crow M T, Gottlieb R A. TAT protein transduction into isolated perfused hearts: TAT-apoptosis repressor with caspase recruitment domain is cardioprotective. Circulation. 2002, 6; 106(6): 735-739.
4. O'Grady J G, Schalm S W, Williams R (1993). "Acute liver failure: redefining the syndromes". Lancet 342 (8866): 273-275.
5. Nagahara H, et al. Transduction of full-length TAT fusion proteins into mammalian cells: TAT-p27Kip1 induces cell migration. Nat Med. 1998; 4(12):1449-52.
6. Becker-Hapak M & Dowdy S F. Protein transduction: generation of full-length transducible proteins using the TAT system. Curr Protoc Cell Biol. 2003 May; Chapter 20: Unit 20.2.
7. Ho A, et al. Synthetic protein transduction domains: enhanced transduction potential in vitro and in vivo. Cancer Res. 2001; 61(2):474-7.
8. Schwarze S R, et al. In vivo protein transduction: delivery of a biologically active protein into the mouse. Science. 1999; 285(5433):1569-72.
9. Rapoport M, et al. TAT-based drug delivery system—new directions in protein delivery for new hopes? Expert Opin Drug Deliv. 2009; 6(5):453-63.
10. Sandra Console, et al Antennapedia and HIV Transactivator of Transcription (TAT) "Protein Transduction Domains" Promote Endocytosis of High Molecular Weight Cargo upon Binding to Cell Surface Glycosaminoglycans. THE JOURNAL OF BIOLOGICAL CHEMISTRY, 2003; 278:35109-35114.
11. Hirofumi Noguchi, et al. PDX-1 Protein Containing Its Own Antennapedia-Like Protein Transduction Domain Can Transduce Pancreatic Duct and Islet Cells. DIABETES. 2003; 52:1732-1737.
12. M. Cristina Cardoso & Heinrich Leonhardt. Protein transduction: A novel tool for tissue regeneration. Biol Chem. 2002; 383:1593-1599.
13. Said Hassane et al. Cell penetrating peptides: overview and applications to the delivery of oligonucleotides, Cell Mol Life Sci. 2010; 67(5): 715-26. Review.

FIGURES

FIG. 1:
TAT-ARC and TAT-βgal treated mice underwent a procedure of partial hepatic ischemia lasting for 60 minutes, which was followed by reperfusion. Serum AST (a) and ALT (b) levels were measured at the indicated time points before the procedure and after reperfusion as markers for liver injury. Values are mean±SD for independent animals (n=7-8).

Figure 2:
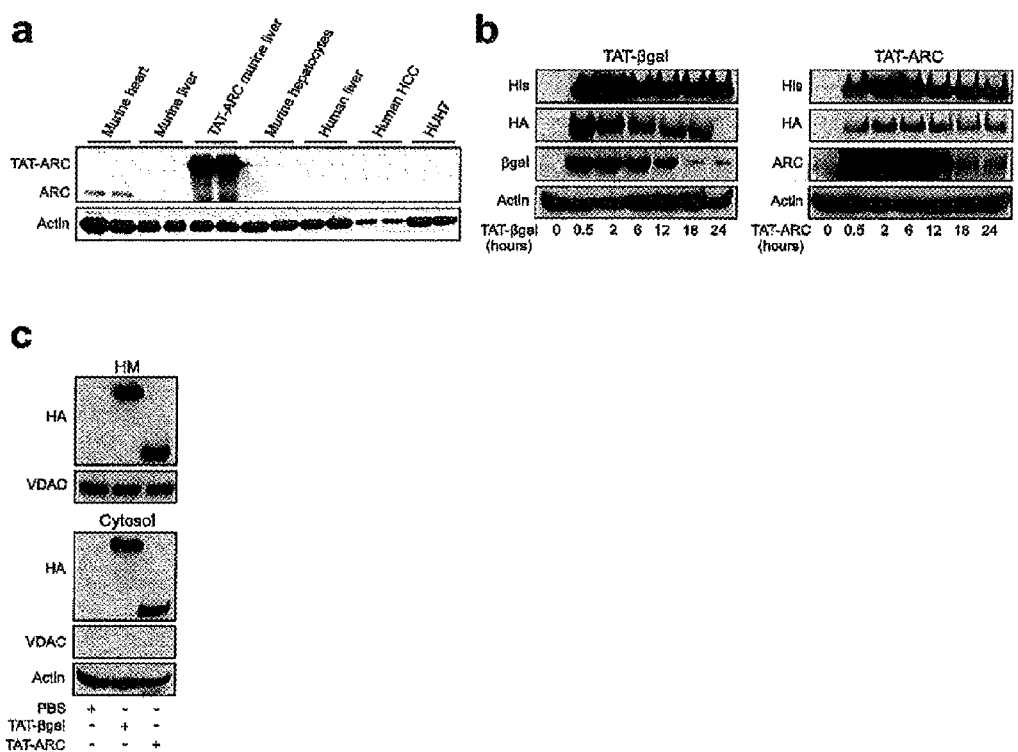

FIG. 2:
Endogenous and ectopic ARC expression following PTD-ARC protein transduction with TAT-ARC. (a) Western analysis of endogenous ARC protein expression in various hepatic cells and tissues. Protein lysates from selected cells/tissues were processed for Western blot analysis and probed with a polyclonal antibody to ARC. Lysate from heart muscle and TAT-ARC protein transduced to murine liver was used as positive control. (b) Time course of TAT-βgal and TAT-ARC protein expression detected by immunoblot following intraperitoneal protein transduction. Membranes were probed with antibodies as indicated. (c) Western blot of subcellular fractions showing TAT-ARC protein transduction to mitochondria (HM) and cytosol.

Figure 3:
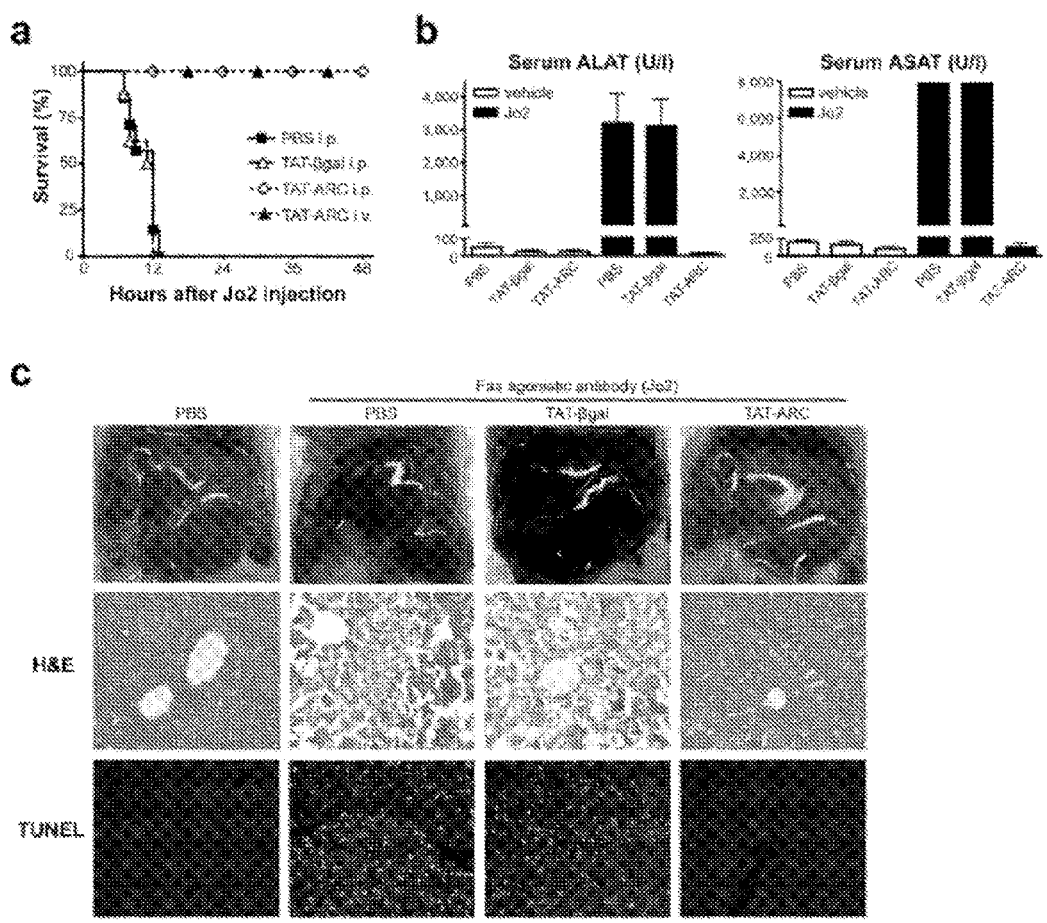

FIG. 3:
TAT-ARC prevents liver failure induced by Fas-agonistic antibody. (a) Serum levels of ALAT and ASAT 6 hours after Fas agonist treatment (n=5-7 per group, data are mean±SEM). (b) TAT-ARC prevents Fas-agonistic antibody (Jo2, 0.5 mg/kg i.v.) induced liver failure (n=6-8 per group). TAT-ARC i.v. (20 mg/kg) was given 1 hour after Jo2 injection. (c) Liver appearance, H&E staining, and TUNEL assay 6 hours following Jo2 treatment. TAT-ARC mediated inhibition and prevention of liver cell death in otherwise necrotic livers is visualized in photographs, hematoxylin eosin stains, and TUNEL-stained immunofluorescent liver sections following Fas (Jo2) stimulation.

Figure 4:
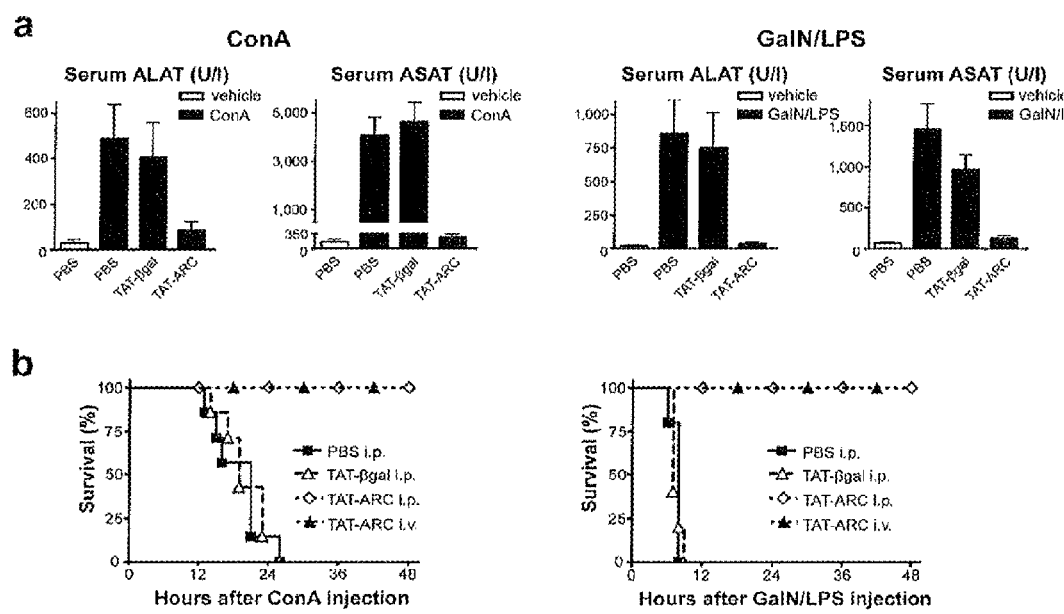

FIG. 4:
TAT-ARC protein transduction protects from TNF-alpha-mediated liver failure induced by ConA and GalN/LPS. (a) Serum levels of ALAT and ASAT 12 hours after ConA and 6 hours after GalN/LPS treatment (n=5-7 per group, data are mean±SEM). (b) TAT-ARC prevents ConA (30 mg/kg i.v.) induced liver failure (n=6-8 per group). TAT-ARC i.v. (20 mg/kg) was given 2 hours after ConA injection. TAT-ARC prevents GalN/LPS (700 mg/kg/35 μg/kg i.p.) induced liver failure (n=5 per group). TAT-ARC i.v. (20 mg/kg) was given 15 minutes after GalN/LPS injection.

FIG. 5:
TAT-ARC prevents APAP-induced liver failure. (a) Serum levels of ALAT and ASAT 20 hours after APAP (300 mg/kg i.p.) treatment (n=5-6 per group, data are mean±SEM). (b) TAT-proteins and vehicle were given 1 hour before APAP (500 mg/kg i.p.) and then every 12 hours for 3 days.

TAT-ARC+1 i.p. was given 1 hour after APAP injection (n=2) and then every 12 hours for 3 days.

SEQUENCES

SEQ ID NO. 1: ARC polynucleotide (DNA) sequence (CDS, coding)
SEQ ID NO. 2: ARC polypeptide (protein) sequence (1-208)
SEQ ID NO. 3: ARC 149D polynucleotide (DNA) sequence (pseudophsophorylated ARC; Zhang & Herman, Journal of Cellular Biochemistry 2006)
polynucleotide (DNA) sequence (CDS, coding)
SEQ ID NO. 4: ARC 149D polypeptide (protein) sequence (1-208)
SEQ ID NO. 5: KR3 ARC polynucleotide (DNA) sequence (proteasomal degradation resistant ARC; Nam et al., JBC 2007)
polynucleotide (DNA) sequence (CDS, coding)
SEQ ID NO. 6: KR3 ARC polypeptide (protein) sequence (1-208)
SEQ ID NO. 7: KR3 ARC 149D polynucleotide (DNA) sequence (pseudophosphorylated, non degradable ARC), polynucleotide (DNA) sequence (CDS, coding)
SEQ ID NO. 8: KR3 ARC 149D polypeptide (protein) sequence (1-208)
SEQ ID NO. 9: TAT-ARC polynucleotide (DNA) sequence: comprises a bacterial promoter, a His-tag, TAT, HA-tag, ARC, and stop codon
SEQ ID NO. 10: TAT-ARC polypeptide (protein) sequence:
SEQ ID NO. 11: HIV TAT polynucleotide sequence:
SEQ ID NO. 12: HIV TAT polypeptide (protein) sequence
SEQ ID NO. 13: TAT-ARC polynucleotide sequence
SEQ ID NO. 14: TAT-ARC polypeptide (protein) sequence
SEQ ID NO. 15: TAT protein transduction domain amino acid sequence (11aa)
SEQ ID NO. 16: TAT protein transduction domain nucleotide sequence (as we used it, 33 nucleotides)
SEQ ID NO. 17: Antennapedia PTD
SEQ ID NO. 18-23: PTD

The invention claimed is:

1. A method for treating liver failure or acute liver failure (ALF), comprising the step of introducing a fusion protein comprising a) an apoptosis repressor with a caspase recruitment domain (ARC), wherein ARC comprises SEQ ID NO:2, SEQ ID NO:4, SEQ ID NO:6 or SEQ ID NO:8, and b) a protein transduction domain (PTD) into a liver cell.

2. The method of claim 1, wherein said PTD comprises a human immunodeficiency virus (HIV) TAT protein transduction domain or an Antennapedia protein transduction domain.

3. The method of claim 1, wherein said PTD is selected from the group consisting of one of SEQ ID NOs:15-23.

4. A method for inhibiting liver cell death comprising exposing a cell to a fusion protein comprising a) an apoptosis repressor with a caspase recruitment domain (ARC), wherein ARC comprises SEQ ID NO:2, SEQ ID NO:4, SEQ ID NO:6 or SEQ ID NO:8, and b) a protein transduction domain (PTD).

5. The method of claim 4, wherein said PTD comprises a human immunodeficiency virus (HIV) TAT protein transduction domain or an Antennapedia protein transduction domain.

6. The method of claim 4, wherein the PTD is selected from the group consisting of one of SEQ ID NOs:15-23.

* * * * *